(12) United States Patent
Bernardini et al.

(10) Patent No.: US 8,440,213 B2
(45) Date of Patent: May 14, 2013

(54) PESTICIDES FORMULATIONS

(75) Inventors: Marco Bernardini, Lodi (IT); Francesca Borgo, Milan (IT); Luigi Capuzzi, Novara (IT); Pietro Domenichini, Milan (IT); Giorgio Freschi, Piacenza (IT)

(73) Assignee: SIPCAM. S.p.A., Milan (IT)

( * ) Notice: Subject to any disclaimer, the term of this patent is extended or adjusted under 35 U.S.C. 154(b) by 175 days.

(21) Appl. No.: 13/221,346

(22) Filed: Aug. 30, 2011

(65) Prior Publication Data

US 2011/0312496 A1    Dec. 22, 2011

Related U.S. Application Data

(62) Division of application No. 10/547,612, filed as application No. PCT/EP2004/001906 on Feb. 26, 2004, now Pat. No. 8,029,813.

(30) Foreign Application Priority Data

Mar. 6, 2003  (IT) .............................. MI2003A0411

(51) Int. Cl.
*A01N 25/00* (2006.01)
*A01N 25/04* (2006.01)
*A01N 25/26* (2006.01)

(52) U.S. Cl.
USPC ............ 424/405; 504/363; 504/364; 504/100

(58) Field of Classification Search ........................ None
See application file for complete search history.

(56) References Cited

U.S. PATENT DOCUMENTS

| | | | | | |
|---|---|---|---|---|---|
| 3,920,680 | A | * | 11/1975 | Golyshin et al. ............ | 548/308.4 |
| 5,262,420 | A | * | 11/1993 | Terada et al. ................ | 514/277 |
| 5,266,590 | A | | 11/1993 | Narayanan | |
| 5,527,823 | A | | 6/1996 | Martin et al. | |
| 5,843,982 | A | * | 12/1998 | Leadbitter ................... | 514/422 |
| 5,905,072 | A | * | 5/1999 | Capuzzi et al. .............. | 514/63 |
| 6,797,301 | B1 | | 9/2004 | Duvert et al. | |

FOREIGN PATENT DOCUMENTS

| | | |
|---|---|---|
| EP | 0 533 057 A | 3/1993 |
| EP | 0 729 700 A | 9/1996 |
| EP | 1 608 220 B1 | 12/2010 |
| JP | 01 197403 A | 8/1989 |
| WO | WO 02/45507 A | 6/2002 |

OTHER PUBLICATIONS

Database WPI Section Ch, Week 198938; Derwent Publications Ltd., London, GB; Class A97, AN 1989-273339, 1989.
Allen F.M. Barton, "Solubility Parameters", Chemical Reviews, vol. 75, No. 6, 1975, pp. 731-753.
W.C. Griffin, "Classification of Surface-Active Agents by "HJB"", Journal Society Cosmetic Chemists 1, 311-326, 1949.
An English language abstract of JP1-197403.

* cited by examiner

*Primary Examiner* — David J Blanchard
*Assistant Examiner* — Tigabu Kassa
(74) *Attorney, Agent, or Firm* — Arent Fox LLP

(57) ABSTRACT

Concentrated microemulsions comprising: 1) 10-25 parts by weight of a pesticide with a solubility in water at 20° C. lower than 1% l by weight and having a melting point from 10° C. to 60° C.; 2) 8-25 parts by weight of one or more solvents containing oxygen atoms, having a solubility in water at 20° C. lower than 5% by weight and the Hildebrand solubility parameter in the range 16-21 $MPa_{1/2}$; 3) 10-20 parts by weight of a polyol; 4) 10-25 parts by weight of one or more non ionic surfactants having a HLB value from 9 to 15; 5) 2-10 parts by weight of one or more anionic surfactants; 6) water up to 100 parts by weight; wherein—the ratio by weight between 2) and 1) ranges from 0.8:1 to 1.5:1;—the ratio by weight between 4) +5) and 1) is in the range 0.5:1-3:1;—the ratio by weight between 4) and 5) ranges from 1:1 to 4.1.

14 Claims, No Drawings

PESTICIDES FORMULATIONS

CROSS-REFERENCE TO RELATED APPLICATION

This application is a divisional of application Ser. No. 10/547,612, filed Sep. 1, 2005, now pending, which is a National Stage entry of International Application Number PCT/EP2004/001906, filed Feb. 26, 2004, claiming the benefit of priority of Italian Patent Application No. MI2003A000411 filed Mar. 6, 2003. The disclosures of these prior applications are hereby incorporated by reference herein in their entirety.

The present invention relates to pesticides formulations with reduced environmental impact, low toxicity and use thereof.

It is well known that pesticides are marketed under the form of concentrated solutions emulsifiable in water comprising the active ingredient, surfactants and aromatic oil-originated solvents with a particular preference for the naphtha solvent. It is well known that the presence of aromatic solvents involves toxicological risks compelling the producer, in view of the law, to classify the formulation as harmful for the user (Symbol $X_n$ and risk phrase R65: "Harmful: may cause lung damage if swallowed") and for the environment. Therefore even non toxic active ingredients are penalized when they are used in said concentrated solutions. The $X_n$ classification of a formulation, requiring for its use a specific authorization, is a strong limitation in product development.

Stable concentrated formulations of agrochemicals, preferred from the toxicological and environmental point of view, are therefore required. These alternative formulations are therefore an object of primary importance from both the technical and commercial point of view.

Stable concentrated formulations of active ingredients without solvents are known. When the active ingredient has a melting point higher than 60° C., formulations in the form of aqueous suspensions are known. When the active ingredient has a melting point lower than 10° C., formulations under the form of aqueous micro or macro emulsions are known.

When the active ingredient has a melting point in the range 10° C.-60° C. the obtainment of stable formulations in concentrated aqueous suspension is very difficult. In fact micronization of the active ingredient is required causing its overheating, originating phase transition and recrystallization phenomena that can compromise the long-term stability of the suspension.

The obtainment of formulations under the form of stable aqueous emulsions or microemulsions of agrochemicals having a melting point in the range 10° C.-60° C. is particularly difficult since the recrystallization risks according to unstable formulations are very frequent.

Agrochemical emulsions with melting points between 10° C. and 60° C. prepared by the Applicant resulted unstable even for small temperature variations. As a matter of fact recrystallization phenomena have been observed.

The need was therefore felt to have available concentrated formulations of pesticides having a melting point in the range 10° C.-60° C. with a reduced environmental impact and low toxicity and stable upon storage without giving recrystallization phenomena, substantially maintaining the same biological activity of the commercial formulations containing aromatic solvents.

The Applicant has surprisingly and unexpectedly found concentrated compositions of crop protection products having a melting point in the range 10° C.-60° C. solving the above technical problem.

An object of the present invention are concentrated microemulsions stable upon time comprising:

1) 10-25 parts by weight, preferably 12-20 parts by weight of a pesticide stable in water having a solubility in water, at 20° C., lower than 1% by weight, having a melting point from 10° C. to 60° C.;
2) 8-25 parts by weight of one or more solvents containing oxygen atoms, having a flash point >60° C., solubility in water at 20° C. lower than 5% by weight, the Hildebrand solubility parameter in the range 16-21 $MPa^{1/2}$;
3) 10-20 parts by weight, preferably 12-18 parts by weight of a polyol soluble in water at 20° C.;
4) 10-25 parts by weight, preferably 12-20 parts by weight of one or more non ionic surfactants having a HLB value (hydrophylic/lipophylic balance) from 9 to 15, preferably from 10 to 13;
5) 2-10 parts by weight, preferably 4-8 of one or more anionic surfactants;
6) 20-40 parts by weight, preferably 25-35 of water;

wherein
the sum of the amounts of the compounds 1), 2), 3), 4), 5), 6) is 100 parts by weight;
the ratio by weight between the amount of solvent 2) and of active ingredient 1) ranges from 0.8:1 to 1.5:1;
the ratio by weight between the sum of the amounts of the surfactants 4) and 5) and the amount of the pesticide 1) is in the range 0.5:1-3:1, preferably 1:1-2:1;
the ratio by weight between 4) and 5) ranges from 1:1 to 4:1.

Said concentrated microemulsions are stable at room temperature for a very long time, even more than 2 years.

The crop protection product component 1) is selected among herbicides, fungicides and insecticides. In particular as herbicides it can be mentioned:

herbicides of the class of chloroacetamides or chloroacetanilides as for example:

|  | Melting point | Solubility |
|---|---|---|
| Alachlor | 40.5-41.5° C. | 170.3 mg/l |
| Propisochlor | 21.6° C. | 184 mg/l |
| Acetochlor | 10.6° C. | 223 mg/l | herbicides of the dinitro aniline class as for example:

|  | | |
|---|---|---|
| Pendimethalin | 54-58° C. | 0.3 mg/l |
| Trifluralin | 43-47.5° C. | 0.4 mg/l | herbicides of the isoxazolidinone class as for example:

|  | | |
|---|---|---|
| Clomazone | 25° C. | 1.1 g/l | herbicides of the hydroxybenzonitrile class as for example:

|  | | |
|---|---|---|
| Bromoxynil octanoate | 45-46° C. | 3 mg/l | herbicides of the aryloxyalkanoic acid class as for example:

| MCPA-thioethyl | 41-42° C. | 2.3 mg/l |
|---|---|---|

As fungicides it can be mentioned:
fungicides of the triazole class as for example:

| Tetraconazole | 30-35° C. | 156 mg/l |
|---|---|---|
| Penconazole | 57.6-60.3° C. | 73 mg/l |

As insecticides it can be mentioned:
insecticides of the class of non ester pyrethroids as for example:

| Etofenprox | 36.4-38° C. | <1 microg/l |
|---|---|---| insecticides of the phosphooraanic class as for example:

| Chlorpyriphos | 42-43.5° C. | 1.4 mg/l |
|---|---|---|
| Methidathion | 39-40° C. | 200 mg/l |

The preferred herbicides are selected among Pendimethalin [N-(1-ethylpropyl)-2,6-dinitro-3,4-xylidine C.N. 40487-42-1]e Trifluralin ($\alpha,\alpha,\alpha$,-trifluoro-2,6-dinitro-N,N-dipropyl-p-toluidine C.N.1582-09-8).

The preferred insecticide is Etofenprox [2-(4-ethoxyphenyl)-2-methylpropyl 3-phenoxybenzyl ether C.N. 80844-07-1].

As solvents component 2) it can be mentioned:
acetals as for example dibutoxy methane(butylal);
alkyl esters of carboxylic acids with the alkyl having $C_4$-$C_{10}$;
alkyl esters of bicarboxylic acids, as for example dimethyl glutarate, dimethyl succinate, dimethyl adipate or mixtures thereof;
alcohols as for example isooctanol.

Preferably the solvent is selected from heptyl acetate, dibutoxy methane and the mixture of the dimethyl esters of glutaric, succinic and adipic acid.

With polyols component 3), compounds having at least 2 hydroxyl groups are meant. As polyols ethylene glycol, propylene glycol, glycerol, preferably propylene glycol can be used.

As nonionic surfactants components 4) those having a cloud point higher than 50° C. are preferred. It can be mentioned polyethoxylated fat alcohols, polyethoxylated castor oil, polyethoxylated distyrylphenols, polyethoxylated tristyrylphenols, polyethoxylated sorbitan esters, alkyl polyglycosides, polyethoxylated-polypropoxylated aliphatic alcohols. There are preferred polyethoxylated castor oil having an ethoxylation number in the range 15-40, preferably 25-35; polyethoxylated distyrylphenols having an ethoxylation number in the range 12-25, preferably 15-20; polyethoxylated tristyrylphenols having an ethoxylation number in the range 15-40, preferably 16-25. Generally said products are under the form of mixtures having a different ethoxylation or propoxylation degree.

As anionic surfactants component 5), alkyl benzen sulphonates, alkyl sulphates, polyethoxylated phosphorylated tristyryl phenols, polyethoxylated sulphated tristyryl phenols, preferably dodecyl benzen calcium sulphonate.

The microemulsions of the present invention can optionally contain additives as for example antioxidant agents, UV stabilizers, pH correctors, antimoulding agents and antifoaming agents. The total amount of said additives is generally lower than 2% by weight. Said additives are well known in the prior art.

The process of preparation of the microemulsions of the invention comprises:
the dissolution of the product component 1), optionally heated to a temperature of 40° C.-50° C. to liquify it in the solvent component 2) under mild stirring,
addition under stirring of the surfactants component 4) and 5) and of the polyol component 3) and then of water maintaining the whole under stirring until obtaining the microemulsion, i.e., a macroscopically clear and perfectly homogeneous dispersion.

The said microemulsions consist of particles of less than 200 nanometers size dispersed in an aqueous phase, they have transparent appearance and are stable at −5° C. and at 54° C. for at least 14 days.

The formulations of the present invention show various advantages from the point of view of the user safety and from the environmental point of view. Due to the nature of the solvents used, the formulations are not flammable and, the agrochemical utilized being equal, they are less irritating and less toxic than the analogous commercial formulations containing an aromatic solvent.

A further object of the present invention is a method of control of agronomically remarkable pests comprising the dilution of the microemulsion in water in amounts in the range 0.05-2.5% by weight. The obtained mixtures are directly sprayed on the crops obtaining a pest control at least equal and sometimes significantly improved compared to analogous treatments carried out at equal doses of active ingredient in commercial formulations containing aromatic solvents.

With respect to the commercial product containing the Etofenprox insecticide and aromatic solvents (Trebon), it has been found that the microemulsions of the invention surprisingly show, the dose of Etofenprox being equal, a higher initial activity.

The concentrated microemulsions of the present invention are stable for more than 2 years when stored at room temperature, they are not toxic and irritating whereby they can be handled without inconveniences, in particular they can subsequently be diluted with water and used in crops without damages for the environment and the animals.

Some illustrative Examples follow, which are not limitative of the present invention.

EXAMPLES

Characterization

Hildebrand Solubility Parameter ($MPa^{1/2}$)
It is determined by calculation according to Allan F. M. Barton, in Chemical Review 1975, vol. 76, no. 6, pages 731-753.
Hydrophylic/Lipophylic Balance (HLB)
It is measured or calculated according to Journal Society Cosmetic Chemists 1, 311, (1949) by Griffin, W. C.

Examples 1-9

Preparation of Aqueous Compositions

A weighed amount of pesticide 1), previously heated to 40-50° C., is added to the solvent 2) contained in a vessel equipped with a stirrer, maintaining under stirring until complete dissolution.

Subsequently, under stirring, at room temperature, the surfactant(s), the propylene glycol and finally water are added in sequence.

As active ingredient ETOFENPROX having a purity of 98% by weight was used.

As solvents 2) there were used: EXXATE 700 (heptyl acetate) marketed by Esso having the Hildebrand solubility parameter of 16.5, BUTYLAL (dibutoxy methane) marketed by LAMBIOTTE having the Hildebrand parameter of 16.2, DBE (mixture containing 55-65% of dimethyl glutarate, 15-25% of dimethyl succinate and 10-25% of dimethyl adipate) by Du Pont having the Hildebrand parameter of 20.2 and isooctanol having the Hildebrand parameter of 21.

As polyol 3) the mono propylene glycol was used.

As nonionic surfactant 4) it was used a mixture of polyethoxylated distyryl and tristyryl phenols with 17 ethoxylation moles (EMULSON AG 17A marketed by Cesalpinia Chemicals), polyethoxylated castor oil with 29 ethoxylation moles (ETOCAS 29 marketed by Croda), polyethoxylated tristyrylphenol with 16 ethoxylation moles (SOPROPHOR BSU marketed by Rhodia).

As anionic surfactant 5) calcium dodecylbenzensulphonate was used.

The amounts by weight of the various components 1), 2), 3), 4), 5) are reported in Table 1.

All the compositions of the Examples from 1 to 9 are microemulsions having the characteristics reported in Table 2. In Table 2 it is reported the microemulsion appearance, the active ingredient titre, the pH determined at a dilution of 1% in water.

Furthermore in Table 2 it is reported the appearance of the emulsions obtained by diluting the microemulsion at 5% in water, and then maintained at 30° C. for 2 hours.

The stability of the microemulsions of Table 1 has been evaluated under the following conditions:

a) at cold, modifying in a more restrictive way the standard test CIPAC MT 39.3 (storage for 7 days at 0° C.), evaluating the product after 14 days at −5° C.;

b) at high temperatures, according to the standard test CIPAC MT 46 which requires the storage of the formulation for 14 days at 54° C.

In both cases the microemulsions object of the present invention have maintained unchanged the initial characteristics reported in Table 2.

The above tests are indicative that the so prepared microemulsions are stable under the normal storage conditions for long periods of time and resist even under tropical conditions. The microemulsion of the Example 1, for example, has resulted stable even after 24 months.

TABLE 1

| Component | 1 | 2 | 3 | 4 | 5 | 6 | 7 | 8 | 9 |
|---|---|---|---|---|---|---|---|---|---|
| 1) ETOFENPROX (98%) | 15.3 | 15.3 | 15.3 | 15.3 | 10.2 | 15.3 | 20.4 | 15.3 | 15.3 |
| 2) EXXATE 700 | — | — | — | — | — | 15 | 20 | — | — |
| BUTYLAL | 15 | 15 | 15 | 15 | 10 | — | — | — | — |
| DBE | — | — | — | — | — | — | — | 15 | 15 |
| ISOOCTANOL | 7.3 | 7.3 | 6.1 | — | — | 7.3 | 5.9 | — | 6.1 |
| 3) MONOPROPYLENE GLYCOL | 15 | 15 | 15 | 15 | 15 | 15 | 13 | 15 | 15 |
| 4) EMULSON AG 17A | 15 | — | — | 20 | 20 | 15 | 10 | 17 | 12.5 |
| ETOCAS 29 | — | 15 | 12.5 | — | — | — | — | — | — |
| SOPROPHOR BSU | 2.2 | 2.2 | 1.9 | — | — | 2.2 | 1.8 | — | 1.9 |
| 5) DDBS-Ca | 5.4 | 5.4 | 4.5 | 7 | 7 | 5.4 | 4.3 | 5.5 | 4.5 |
| 6) Water | 24.8 | 24.8 | 29.7 | 27.7 | 37.8 | 24.8 | 24.6 | 32.2 | 29.7 |

TABLE 2

| Example No. | 1 | 2 | 3 | 4 | 5 | 6 | 7 | 8 | 9 |
|---|---|---|---|---|---|---|---|---|---|
| Microemulsion appearance | limpid | limpid | limpid | limpid | limpid | limpid | limpid | limpid | limpid |
| Titre (%) | 14.8 | 15.2 | 15.1 | 15.0 | 9.9 | 15.1 | 20.2 | 14.9 | 15 |
| pH (1% in water) | 5.7 | 8.2 | 8.1 | 6.2 | 6.3 | 5.9 | 6.1 | 5.6 | 5.9 |
| Appearance after dilution at 5% in water | limpid | milky | milky | limpid | limpid | limpid | limpid | limpid | limpid |
| Appearance after dilution at 5% in water after 2 h at 30° C. | limpid | nps | nps | limpid | limpid | limpid | limpid | limpid | limpid | nps = no phase separation

Examples 10-11 (Comparative)

Example 8 was repeated except that instead of DBE solvent the biodiesel solvents (mixture of methyl esters of mainly oleic and linoleic fat acids) having the Hildebrand parameter equal to 14, and N-methyl pyrrolidone having the Hildebrand solubility parameter equal to 23 were respectively used.

No microemulsion was obtained and it was observed the formation of mixtures with rapid tendency to the phase separation.

Application Tests

Field Tests

Example 12

The Example relates to a field test carried out using the formulation of the Example 1 diluted in water at 0.093% by weight to evaluate the agronomical efficacy of the formulation on Leaf Hopper Green (Empoasca Decipiens) on grapevine, in comparison with untreated grapevine.

The field test was carried out at Ormelle (TV) Italy on grapevine plants, *Pinot Grigio* variety, 7 years old, infested by Green Leaf Hopper, grouped in 8 plots of 15 m² each, randomly placed in the vineyard, avoiding zones having borders or unrepeatable characteristics.

The treatment was carried out on four plots with a dose of 140 g/ha of active ingredient Etofenprox corresponding to the label application rate of commercial formulations of Etofenprox.

The agronomical efficacy has been evaluated by counting the number of live insects on 50 leaves, after 15 days after the treatment and comparing it with the number of insects on the untreated plots.

The efficacy is expressed as reduction percentage of the insect number with respect to the number of insects of the untreated plots.

|  | N° insects after 15 days from the treatment | % efficacy 15 days after the treatment | Phytotoxicity |
| --- | --- | --- | --- |
| Composition 1 | 0 | 100 | 0 |
| Untreated | 16 | 0 | 0 |

The product object of the present invention results to be non phytotoxic and perfectly effective.

Example 13

The Example reported below relates to a field test carried out by using the formulation of the Example 1 diluted in water at 0.112% by weight to evaluate the initial activity of the formulation against *aphis gossipi* on melon, in comparison with melons treated with the commercial formulation Trebon® containing the same insecticide Etofenprox and solvents, the application rate of the insecticide being equal.

The field test was carried out at Erbè (VR) Italy on baggio melon plants infested by *aphis gossipi*, grouped in 12 plots each of 15 m², placed in a randomized way in the field, avoiding border zones or with unrepeatable characteristics.

Four plots were treated with the diluted formulation of the Example 1 and other four plots were treated with the commercial formulation Trebon®, using a dose of 168 g/ha of active ingredient Etofenprox.

In the Table below it is reported the number of live insects for plant leaf of the plots treated with the invention formulation with respect to those treated with Trebon or untreated and the respective agronomical efficacy expressed as reduction percentage of the number of insects with respect to the number of insects of the untreated control plots.

|  | No. insects after 4 days from the treatment | % efficacy after 4 days from the treatment | No. insects after 9 days from the treatment | % efficacy after 9 days from the treatment | No. insects after 16 days from the treatment | % efficacy after 16 days from the treatment |
| --- | --- | --- | --- | --- | --- | --- |
| Composition 1 | 3.77 | 31 | 1.53 | 80 | 42.10 | 28 |
| Trebon | 4.52 | 17 | 1.98 | 74 | 31.35 | 46 |
| Untreated control | 5.42 | — | 7.58 | — | 58.26 | — |

The product object of the present invention shows a higher insecticide activity in comparison with the commercial formulation up to 9 days after the treatment.

Example 14

The Example reported below relates to a field test carried out by using the formulation of the Example 1 diluted in water at 0.056% by weight to evaluate the initial activity of the formulation on potato beetle on potato (*leptinotersa decunlineata*), *primura* variety, in comparison with potatoes treated with the commercial formulation Trebon containing the same insecticide Etofenprox and solvents, the application rate of the insecticide being equal.

The field test was carried out at Salerano sul Lambro (LO) Italy on *primura* potato plants infested by potato beetles, grouped in 12 plots each of 10 m², placed in a randomized way in the field, avoiding border zones or with unrepeatable characteristics.

Four plots were treated with the diluted formulation of the Example 1 and other four plots were treated with the commercial formulation Trebon®, using a dose of 84 g/ha of active ingredient Etofenprox. Said treatment was repeated after 9 days.

In the Table it is reported the average number of live larvae of first age for plot of the plots treated with the invention formulation compared to the plots treated with Trebon or untreated and the respective agronomical efficacy expressed in reduction percentage of the number of live larvae of first age in comparison to the average number of the first age larvae of the untreated plots.

| | No. larvae after 1 day from the 1° treatment | % efficacy after 1 day from the 1° treatment | No. larvae after 5 days from the 1° treatment | % efficacy after 5 days from the 1° treatment | No. larvae after 3 days from the 2° treatment | % efficacy after 3 days from the 2° treatment |
|---|---|---|---|---|---|---|
| Composition 1 | 0.62 | 95 | 16.70 | 52 | 2.79 | 84 |
| Trebon | 3.55 | 72 | 13.08 | 62 | 4.34 | 75 |
| Untreated control | 12.58 | — | 34.56 | — | 17.14 | — |

The product object of the present invention shows a higher initial insecticide activity in comparison with the commercial formulation as it results from the values reported in column 2 and in column 6.

Example 15

The Example reported below relates to a field test carried out by using the formulation of the Example 1 diluted in water at 0.1% by weight to evaluate its insecticidal efficacy against *Cydia funebrana* (first larval generation) on plum in comparison with plums treated with commercial product Trebon, the application rate of the insecticide being equal.

The field test was carried out at Riolo Terme (RA)—Italy on plums, President variety, planted in 1991, of 2.5 m of height, grouped in 12 plots of 84.4 m² area and having 4 plants per plot. Four plots were treated with the diluted formulation of the Example 1 and other four plots were treated with the commercial formulation Trebon®, using a dose of 140 g/ha of Etofenprox.

The flight of *Cydia funebrana* adults in the experimental site has been monitored by using pheromones traps, while eggs and their hatch have been directly and periodically checked on fruits.

Treatments of plants started after having found eggs and recording has been done before the starting of the second generation.

100 random fruits per plot were collected and the number of holes recorded.

In the following Table, percent values of damaged fruits are reported as far as concern:
composition 1
commercial product (Trebon®)
untreated control

| | Damaged fruits (%) | Efficacy (%) |
|---|---|---|
| Composition 1 | 1.25 | 80.29 |
| Commercial product | 2.63 | 57.24 |
| Untreated control | 6.50 | — |

Composition 1 shows better and statistically significant effects compared to untreated control and slightly better result compared to the corresponding commercial product.

The invention claimed is:

1. A stable concentrated microemulsions comprising:
1) 10-25 parts by weight of a pesticide stable in water having a solubility in water at 20° C. lower than 1% by weight and a melting point from 10° C. to 60° C.;
2) 8-25 parts by weight of one or more solvents containing oxygen atoms having a flash point >60° C., solubility in water at 20° C. lower than 5% by weight, and a Hildebrand solubility parameter in a range of 16-21 MPa$^{1/2}$;
3) 10-20 parts by weight of a polyol soluble in water at 20° C.;
4) 10-25 parts by weight of one or more nonionic surfactants having a hydrophylic/lipophylic balance (HLB) value from 9 to 15;
5) 2-10 parts by weight of one or more anionic surfactants; and
6) 20-40 parts by weight of water;
wherein the sum of the amounts of the components 1), 2), 3), 4), 5), and 6) is 100 parts by weight; the ratio by weight of the solvent 2) to the pesticide 1) ranges from 0.8:1 to 1.5:1; the ratio by weight of the sum of the amounts of the surfactants 4) and 5) to the amount of the pesticide 1) ranges from 0.5:1 to 3:1; the ratio by weight of 4) to 5) ranges from 1:1 to 4:1; and wherein the one or more solvents 2) are selected from the group consisting of: acetals, alkyl esters of carboxylic acids with the alkyl comprised between $C_4$-$C_{10}$, alkyl esters of bicarboxylic acids, mixtures of alkyl esters of bicarboxylic acids, and alcohols, wherein the microemulsions are stable at −5° C. and 54° C. for at least 14 days and at room temperature for more than two years.

2. The stable concentrated microemulsions according to claim 1, wherein the pesticide is present in an amount of 12-20 parts by weight; the polyol is present in an amount of 12-18 parts by weight; the one or more nonionic surfactants are present in an amount of 12-20 parts by weight; the one or more nonionic surfactants have an HLB value from 10 to 13; the one or more anionic surfactants are present in an amount of 4-8 parts by weight; the water is present in an amount of 25-35 parts by weight; the ratio by weight of the sum of the amounts of the surfactants 4) and 5) to the amount of the pesticide 1) ranges from 1:1 to 2:1.

3. The stable concentrated microemulsions according to claim 1, wherein the pesticide is selected from the group consisting of herbicides, fungicides and insecticides.

4. The stable concentrated microemulsions according to claim 3, wherein the herbicides are selected from the group consisting of chloroacetamides, chloroacetanilides, dinitro aniline, isoxaazolidinone, hydroxybenzonitrile and aryloxyalcanoic acid classes; fungicides are selected from the triazole class; and the insecticides are selected from the group consisting of non ester pyrethroid and phosphoorganic classes.

5. The stable concentrated microemulsions according to claim 3, wherein the herbicides of the chloroacetamide or chloroacetanilide classes are selected from the group consisting of Alachlor, Propisochlor, and Acetochlor; the herbicides of the dinitro aniline class are selected from the group consisting of Pendimethalin, and Trifluralin; the herbicides of the isoxaazolidincne class are selected from Clomazone; the herbicides of the hydroxybenzonitrile class are selected from Bromoxynil octanoate; the herbicides of the class of the aryloxyalkanoic acids are selected from MCPAthioethyl; the fungicides of the triazole class are selected from the group consisting of Tetraconazole and Penconazole; the insecticide of the non ester pyrehtroid class is Etofenprox; and the insecticides of the phosphoorganic class are selected from the group consisting of Chlorpyriphos and Methidathion.

6. The stable concentrated microemulsions according to claim 5, wherein the pesticide 1) is selected from the group consisting of N-(l-ethylpropyl) -2, 6-dinitro-3,4-xylidine, a, a, a, -trifluoro-2, 6-dinitro—N, N—dipropyl- p-toluidine and 2-(4-ethoxyphenyl)-2-methylpropyl-3- phenoxybenzyl ether (Etofenprox).

7. The stable concentrated microemulsions according to claim 1, wherein the one or more solvents 2) is selected from the group consisting of heptyl acetate, dibutoxy methane and the dimethyl esters of glutaric, succinic and adipic acid.

8. The stable concentrated microemulsions according to claim 1, wherein the polyol 3) is selected from the group consisting of ethylene glycol, propylene glycol, and glycerol.

9. The stable concentrated microemulsions according to claim 1, wherein the one or more nonionic surfactants 4) are selected from the group consisting of polyethoxylated fat alcohols, polyethoxylated castor oil, polyethoxylated distyrylphenols, polyethoxylated tristyrylphenols, polyethoxylated sorbitan esters, alkyl polyglycosides, polyethoxylated-polypropoxylated aliphatic alcohols.

10. The stable concentrated microemulsions according to claim 9, wherein the one or more nonionic surfactants 4) are selected from the group consisting of polyethoxy!ated castor oil having an ethoxylation number in a range 15-40, polyethoxylated distyrylphenols having an ethoxylation number in a range 12-25, polyethoxylated tristyrylphenols having an ethoxylation number in a range 15-40, and mixtures thereof.

11. The stable concentrated microemulsions according to claim 10 wherein the one or more nonionic surfactants 4) are selected from the group consisting of polyethoxylated castor oil having an ethoxylation number in a range 25-35, polyethoxylated distyrylphenols having an ethoxylation number in a range 15-20, polyethoxylated tristyrylphenols having an ethoxylation number in a range 16-25, and mixtures thereof.

12. The stable concentrated microemulsions according to claim 1 wherein the anionic surfactants 5) are selected from the group consisting of alkyl benzene sulphonates, alkyl sulphates, polyethoxylated phosphorylated tristyryl phenols, and polyethoxylated sulphated tristyryl phenols.

13. The stable concentrated microemulsions according to claim 12, wherein the anionic surfactants 5) is dodecyl benzene calcium sulphonate.

14. The stable concentrated microemulsions according to claim 1, wherein the microemulsions further comprise one or more additives selected from the group consisting of antioxidant agents, UV stabilizers, pH correctors, antimould agents.

* * * * *